(12) United States Patent
Omori et al.

(10) Patent No.: US 6,479,707 B2
(45) Date of Patent: Nov. 12, 2002

(54) PROCESS FOR PRODUCING 2-BUTANONE AND 2-BUTANOL

(75) Inventors: Hideki Omori, Ichihara (JP); Kazuhiko Haba, Ichihara (JP)

(73) Assignee: Maruzen Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 10/012,318

(22) Filed: Dec. 12, 2001

(65) Prior Publication Data

US 2002/0123654 A1 Sep. 5, 2002

(30) Foreign Application Priority Data

Dec. 22, 2000 (JP) .......................... 2000-390667

(51) Int. Cl.[7] .................. C07B 41/04; C07B 41/02; C07C 45/00; C07C 27/10
(52) U.S. Cl. ................... 568/398.8; 568/401; 568/402; 568/406; 568/910; 568/910.5
(58) Field of Search .................. 568/398.8, 401, 568/402, 406, 910, 910.5

(56) References Cited

U.S. PATENT DOCUMENTS

| 5,294,739 | A | | 3/1994 | Kraushaar-Czarnetzki et al. |
|---|---|---|---|---|
| 5,345,011 | A | * | 9/1994 | Durante et al. |
| 6,020,533 | A | * | 2/2000 | Lewis et al. |
| 6,160,183 | A | * | 12/2000 | Druliner et al. |

FOREIGN PATENT DOCUMENTS

WO     94/17021     8/1994

* cited by examiner

*Primary Examiner*—Johann Richter
*Assistant Examiner*—Sikarl A. Witherspoon
(74) *Attorney, Agent, or Firm*—Oblon, Spivak, McClelland, Maier & Neustadt, P.C.

(57) ABSTRACT

The present invention provides a process for producing 2-butanone and 2-butanol under comparatively mild conditions with a decreased number of steps by direct oxidization of a hydrocarbon, which is cheaper than butenes, as a raw material using molecular oxygen such as air. The process for producing 2-butanone and 2-butanol comprises directly oxidizing n-butane using molecular oxygen in the presence of aluminum phosphate containing transition metal atoms and a selectivity-improving agent, as required.

17 Claims, No Drawings

PROCESS FOR PRODUCING 2-BUTANONE AND 2-BUTANOL

BACKGROUND OF THE INVENTION

1. Field of the Invention

The present invention relates to a process for producing 2-butanone and 2-butanol by directly oxidizing n-butane using molecular oxygen.

2 Background Art

2-Butanone is conventionally produced by synthesizing 2-butanol and dehydrogenating the resulting 2-butanol. As a process for producing 2-butanol used as the raw material, hydration of 1-butene or 2-butene which is a lower olefin is known.

As the hydration process of the butenes, an indirect hydration process in which sulfuric acid is added to the double bond of an olefin and the resulting product is subjected to hydrolysis, and a direct hydration process in which the double bond of an olefin is subjected to hydration using a catalyst as disclosed in Japanese Patent Publication No. 62-61573 and the like are known.

However, the indirect hydration process using sulfuric acid gives rise to problems such as an increase in the number of steps consisting of sulfuric acid absorption, sulfonation, hydrolysis, and separation/concentration, corrosion of a reactor due to acids, and disposal of waste sulfuric acid and waste water.

The direct hydration process of butenes does not use sulfuric acid. However, this process requires a high reaction temperature of 120–180° C. and a high pressure of 40–200 bars. Moreover, use of steam for hydration may cause water to be mixed into the reaction system.

SUMMARY OF THE INVENTION

Accordingly, an object of the present invention is to produce 2-butanone and 2-butanol under comparatively mild conditions with a decreased number of steps by directly oxidizing a raw material hydrocarbon, which is cheaper than butenes, using molecular oxygen such as air.

As a result of extensive studies to attain the above object, the present inventors have found that 2-butanone and 2-butanol can be obtained at a lower temperature and a lower pressure with a decreased number of steps by directly oxidizing n-butane or a hydrocarbon mixture containing n-butane, which is cheap and conventionally used as a fuel, as the raw material using molecular oxygen in the presence of a specific catalyst. This finding has led to the completion of the present invention.

Specifically, the present invention provides a process for producing 2-butanone and 2-butanol comprising directly oxidizing n-butane using molecular oxygen in the presence of aluminum phosphate containing transition metal atoms.

In the production process of the present invention, a selectivity improving agent may be allowed to be present in combination.

DETAILED DESCRIPTION OF THE INVENTION AND PREFERRED EMBODIMENT

In the production process of the present invention, n-butane or a hydrocarbon containing n-butane is used as the raw material. As the hydrocarbon containing n-butane, a butane-butene fraction, produced from a petrochemical unit as a by-product, or a residual fraction obtained by removing butenes from the butane-butene fraction are suitably used. Butenes and the like may remain in these fractions used as the raw material. However, if the n-butane content is too small, the ratio of by-products increases. Therefore, the n-butane content in these fractions is preferably 60 weight % or more, and particularly preferably 80 weight % or more.

As molecular oxygen used for oxidization, high-purity oxygen gas or air, mixed gas in which high-purity oxygen gas or air is diluted with nitrogen, helium, argon, methane, or the like may be used.

Aluminum phosphate containing transition metal atoms used in the process of the present invention acts as a catalyst component. This aluminum phosphate consists of an aluminum atom, phosphorus atom, and oxygen atom as essential components, or further contains a silicon atom or magnesium atom in combination with these atoms. The aluminum phosphate containing an aluminum atom, phosphorus atom, and oxygen atom as the essential components is shown by AlPO-m (m is an integer showing a crystalline type), wherein the ratio of aluminum atoms, phosphorus atoms, and oxygen atoms is approximately 1:1:4. The aluminum phosphate containing a silicon atom or magnesium atom in combination with an aluminum atom, phosphorus atom, and oxygen atom is shown by SAlPO-n or MAlPO-n (n is an integer showing a crystalline type), in which part of the aluminum atoms is replaced by a silicon atom or magnesium atom. The ratio of the sum of aluminum atoms and silicon atoms or magnesium atoms, phosphorus atoms, and oxygen atoms is approximately 1:1:4.

In the process of the present invention, the aluminum phosphate containing transition metal atoms used as the catalyst component is a compound in which part of the aluminum atoms of the above aluminum phosphate is replaced by one or more types of transition metal atoms. This means that transition metal atoms are not merely bonded to the aluminum phosphate physically.

There are no specific limitations to the transition metal atoms replacing the aluminum atom in the aluminum phosphate insofar as its valence change due to electron transfer during oxidation-reduction is one or more. Therefore, copper, titanium, vanadium, iron, cobalt, manganese, chromium, and the like can be given as examples of such transition metals. Of these, vanadium, manganese, cobalt, and copper are particularly preferable.

The amount of transition metal atoms included in the aluminum phosphate is determined so that the percentage of the amount of transition metal atoms in the total amount of transition metal atoms and aluminum atoms is 0.01–20 mol %, and preferably 0.01–10 mol %. If the amount of transition metal atoms exceeds the upper limit, heat stability or crystallinity of the catalyst may decrease. If the amount of transition metal atoms is less than the lower limit, sufficient catalytic activities may not be obtained.

The aluminum phosphate containing transition metal atoms is porous, which is a kind of molecular sieve. This aluminum phosphate has a crystal structure ranging from nearly amorphous to crystalline. The aluminum phosphate, which has any type of the above crystal structures may be used as the catalyst. Of these, porous crystalline aluminum phosphate with a pore diameter of 3–10 angstroms is preferable from the viewpoint of catalytic activities, selectivity of the objective product, and heat stability of the catalyst.

In the production process of the present invention, the amount of the aluminum phosphate containing transition metal atoms used as the catalyst is 0.01–10 weight %, and preferably 0.02–1 weight % of n-butane used as the raw material.

In the present invention, oxidization may be carried out using a batch-type or continuous-type liquid phase process. As the type of reactor, any of a bubble tower-type, stirring-type, circulation-type, and stirring/circulation-type may be employed. The reaction temperature is 50–150° C., and preferably 80–130° C. If the temperature is less than the lower limit, sufficient activities ay not be obtained. If the temperature exceeds the upper limit, the amount of by-products such as butenes, acetaldehyde, acetic acid, acetone, and carbon dioxide or the amount of decomposition products increases. The reaction pressure is from atmospheric pressure to 10 MPa, and preferably 0.5–5 MPa.

In the process of the present invention, a selectivity improving agent may be added to the reaction system in order to improve selectivity. As the selectivity improving agent, water, pyridine, fluorinated hydrocarbons, hydrogen peroxide, and organic peroxides are preferable. Of these, water, pyridine, hydrogen peroxide, and fluorinated hydrocarbons such as perfluorooctane are particularly preferable. These selectivity improving agents are added in an amount based on weight from $\frac{1}{100}$ to 50 times, and preferably from $\frac{1}{10}$ to 30 times the amount of the aluminum phosphate containing transition metal atoms.

In the process of the present invention, a mixture of 2-butanone and 2-butanol is obtained from n-butane. The mixture is separated by distillation to obtain a product. 2-Butanol in the resulting mixture may be converted into 2-butanone by dehydrogenation using a dehydrogenation catalyst to obtain a product. 2-Butanone thus obtained is useful as a high performance solvent in various fields such as paint and adhesives. 2-Butanol is useful as a solvent, a raw material for producing 2-butanone, and the like.

EXAMPLES

The present invention is described in more detail by examples and comparative examples, which should not be construed as limiting the scope of the present invention. A conversion of n-butane and a selectivity of the objective products were calculated by the following methods.
(1) Conversion of n-butane The amount of unreacted n-butane was measured using a gas buret. The conversion of n-butane was calculated according to the following equation.

Conversion (mol %) $(A1\text{-}A2)/A1 \times 100$

A1: Amount of raw material n-butane
A2: Amount of unreacted n-butane
(2) Selectivity of objective product The selectivity of the objective products (2-butanone and 2-butanol) was calculated according to the following equation.

Selectivity (mol %) $= B/(A1\text{-}A2) \times 100$

B: Amount of objective product
A1: Amount of raw material n-butane
A2: Amount of unreacted n-butane Reference Example 1

Preparation of Catalyst A

A 1500 ml vessel made of Teflon was charged with 27.3 g of orthophosphoric acid (85%, manufactured by Wako Pure Chemical Industries, Ltd.) and 56. 68 g of aluminum isopropoxide (manufactured by Wako Pure Chemical Industries, Ltd.). The mixture was mixed for one hour. After the addition of 150 ml of methanol, the mixture was mixed for three hours. After the addition of 8.33 g of cataloid silica, the mixture was stirred for three hours. After the addition of 20.4 g of a tetraethylammonium hydroxide aqueous solution (10%, manufactured by Tokyo Kasei Kogyo Co., Ltd.), the mixture was stirred for three hours. After the addition of 3.28 g of a vanadyl sulfate hydrate (tetrahydrate) , the mixture was stirred for one hour. The resulting solution was placed in an autoclave container and subjected to hydrothermal synthesis at 210° C. for 40 hours. After completion of the hydrothermal synthesis, the resulting solid component was washed repeatedly by rinsing and filtration and then dried at 70° C. for 18 hours. The dried product was sintered at 500° C. for five hours in air.

The resulting powder was analyzed by an X-ray diffraction method. As a result, peaks originating from vanadium oxide and metal vanadium were not confirmed. The diffraction pattern coincided with the diffraction pattern of SAlPO-34 which is one type of aluminum phosphate containing silicon. The vanadium (V) content (V (mol)/(V (mol)+Al (mol)) measured by an ICP emission spectrometry was 4.8 mol %. This catalyst is referred to as a catalyst A and indicated by VAlPSO-34.

Reference Example 2

Preparation of Catalyst B

A beaker made of Pyrex glass was charged with 8.29 g of 85% phosphoric acid, 0.3227 g of a cobalt chloride hydrate ($CoCl_2 \cdot 6H_2O$), and 52.11 g of ion-exchange water. The mixture was stirred while cooling with ice until a homogenous solution was obtained. After the addition of 4.87 g of boehmite ("PURAL SCF55" manufactured by CONDEA), the mixture was stirred while cooling with ice. After the addition of 4.36 g of triethylamine, the mixture was stirred at room temperature for 18 hours. The resulting solution was placed in an autoclave container provided with Teflon coating and subjected to hydrothermal synthesis at 175° C. for 72 hours. After completion of the hydrothermal synthesis, the resulting product was washed repeatedly by rinsing and filtration and dried at 80° C. for 18 hours to obtain a blue powder. The resulting powder was sintered at 550° C. for 16 hours to obtain a green powder.

The resulting green powder was analyzed by using an X-ray diffraction system. As a result, peaks originating from a transition metal and a transition metal oxide were not confirmed. The diffraction pattern coincided with the diffraction pattern of AlPO-5 which is one type of aluminum phosphate. The cobalt (Co) content (Co (mol)/(Co (mol)+Al (mol))) measured by ICP mission spectrometry was 6 mol %. This catalyst is referred to as a catalyst B and indicated by CoAlPO-5.

Example 1

A 50 ml autoclave made of stainless steel equipped with an electromagnetic induction stirring rod was charged with 20 mg of the catalyst A (VAlPSO-34) and 4 g of n-butane. The autoclave was filled with pure oxygen gas at room temperature. After heating the mixture to 100° C. in an oil bath, the mixture was allowed to react at a pressure of 4 MPa for 24 hours. After completion of the reaction, residual oxygen gas was removed by trapping the contents of the autoclave in a dry ice-methanol bath at −70° C. Unreacted n-butane was volatilized and removed by trapping the contents of the autoclave in an ice-ethanol bath at 2° C. The components trapped in the ice-ethanol bath were collected and analyzed by gas chromatography.

The conversion of n-butane calculated from the analysis values was 7.9 mol %. The selectivity of 2-butanone and 2-butanol was 52.3 mol %.

Example 2

Oxidation was carried out under the same conditions as in Example 1 except for adding 0.5 g of water as a selectivity improving agent. The reaction results are shown in Table 1.

Examples 3–6

Oxidation was carried out under the same conditions as in Example 2 except for changing the catalyst as shown in Table 1. The reaction results are shown in Table 1.

TABLE 1

| Example | Catalyst Type | Catalyst Formula * | Conversion (mol %) | Selectivity (mol %) |
|---|---|---|---|---|
| 1 | A | VAlPSO-34 | 7.9 | 52.3 |
| 2 | A | VAlPSO-34 | 4.5 | 79.5 |
| 3 | B | CoAlPO-5 | 4.0 | 55.0 |
| 4 | C | CoAlPSO-34 | 1.8 | 60.5 |
| 5 | D | MnAlPSO-34 | 5.9 | 58.3 |
| 6 | E | CuAlPSO-34 | 4.3 | 62.2 |

* V: Vanadium, Co: Cobalt, Mn: Manganese, Cu: Copper

Examples 7-9

Oxidation was carried out under the same conditions as in Example 2 except for changing the selectivity improving agent as shown in Table 2. The reaction results are shown in Table 2.

TABLE 2

| Example | Additive Type | Amount (g) | Conversion (mol %) | Selectivity (mol %) |
|---|---|---|---|---|
| 1 | None | — | 7.9 | 52.3 |
| 7 | Pyridine | 0.02 | 5.8 | 68.1 |
| 8 | Perfluorooctane | 0.02 | 4.9 | 74.2 |
| 9 | Hydrogen peroxide * | 0.5 | 8.1 | 60.2 |

* 30% aqueous solution

According to the present invention, cheap n-butane can be directly oxidized using molecular oxygen by using aluminum phosphate containing transition metals as a catalyst. Therefore, 2-butanone and 2-butanol can be obtained at a relatively lower temperature and lower pressure with a decreased number of steps.

Obviously, numerous modifications and variations of the present invention are possible in light of the above teachings. It is therefore to be understood that, within the scope of the appended claims, the invention may be practiced other than as specifically described herein.

What is claimed is:

1. A process for producing 2-butanone and 2-butanol comprising directly oxidizing n-butane with molecular oxygen in the presence of an aluminum phosphate comprising aluminum, phosphorus, oxygen, silicon, and vanadium, and a selectivity improving agent.

2. The process according to claim 1, wherein the selectivity improving agent is one or more compounds selected from the group consisting of water, pyridine, fluorinated hydrocarbons and hydrogen peroxide.

3. The process according to claim 1, wherein the total amount of vanadium and aluminum in the aluminum phosphate is from 0.01 to 20 mol %.

4. The process of claim 1, wherein the total amount of vanadium and aluminum in the aluminum phosphate is from 0.01 to 10 mol %.

5. The process of claim 1, wherein the aluminum phosphate is present in an amount of 0.01 to 10 wt % based upon the total amount of n-butane.

6. The process of claim 1, wherein the aluminum phosphate is present in an amount of 0.02 to 1 wt % based upon the total weight of the n-butane.

7. The process of claim 1, wherein the oxidization is carried out at a temperature of from 50–150° C.

8. The process of claim 1, wherein the oxidization is carried out at a temperature of from 80–130° C.

9. The process of claim 1, wherein a reaction pressure is from 0.5 to 5 MPa.

10. The process of claim 1, wherein the selectivity improving agent is present in an amount of from $1/100$ to 50 times the amount of the aluminum phosphate.

11. The process of claim 1, wherein the selectivity improving agent is present in an amount of from $1/10$ to 30 times the amount of the aluminum phosphate.

12. The process of claim 1, further comprising distilling the 2-butanone and 2-butanol.

13. The process of claim 1, wherein the selectivity improving agent is water.

14. The process of claim 1, wherein the n-butane comprises at least 60 wt % of n-butane.

15. The process of claim 1, wherein the n-butane comprises at least 80 wt % of n-butane.

16. The process of claim 1, wherein the aluminum phosphate is porous.

17. The process of claim 1, wherein the oxidization is carried out in a bubble tower reactor, stirring reactor, circulation reactor, or stirring/circulation reactor.

* * * * *